United States Patent [19]

Goble et al.

[11] Patent Number: 4,960,420

[45] Date of Patent: Oct. 2, 1990

[54] CHANNEL LIGAMENT CLAMP AND SYSTEM

[76] Inventors: E. Marlowe Goble, 550 E. 1400 North, Suite M; W. Karl Somers, 651 N. 150 West, both of Logan, Utah 84321

[21] Appl. No.: 235,194

[22] Filed: Aug. 23, 1988

[51] Int. Cl.[5] .................... A61F 5/04; A61B 17/04; F16B 15/00
[52] U.S. Cl. ...................... 606/72; 606/75; 606/77; 606/151; 606/154; 411/457
[58] Field of Search ......... 128/92 YC, 92 YD, 92 YJ, 128/334 R, 92 R; 623/13, 16; 411/457, 458, 459, 460, 470, 469; 606/75, 77, 72, 151, 154

[56] References Cited

U.S. PATENT DOCUMENTS

| | | |
|---|---|---|
| 82,181 | 9/1868 | Tileston .......................... 411/470 |
| 431,175 | 7/1890 | Southwick ..................... 411/470 |
| 758,881 | 5/1904 | Yost ................................. 411/457 |
| 1,425,199 | 8/1922 | Hartley ........................... 411/457 |
| 1,598,026 | 8/1926 | Thompson ..................... 411/470 |
| 1,638,477 | 8/1927 | Dyer ............................... 411/470 |
| 1,948,462 | 2/1934 | Page ................................ 411/457 |
| 2,065,325 | 12/1936 | Calhoun ........................ 411/457 |
| 2,134,765 | 11/1938 | Putnam ......................... 411/457 |
| 2,398,603 | 4/1946 | Soderberg ..................... 411/457 |
| 4,047,524 | 9/1977 | Hell ............................... 128/92 YC |
| 4,146,022 | 3/1979 | Johnson ....................... 128/92 YD |
| 4,263,903 | 4/1981 | Griggs .......................... 128/92 YC |
| 4,278,091 | 7/1981 | Borzone ........................ 411/469 |
| 4,400,833 | 8/1983 | Kurland ....................... 128/92 YC |
| 4,414,967 | 11/1983 | Shapiro ........................ 128/92 VT |
| 4,438,769 | 3/1984 | Pratt ............................ 128/92 YC |
| 4,456,006 | 6/1984 | Wevers ........................ 128/92 YC |
| 4,592,346 | 6/1986 | Jurgutis ........................ 411/457 |
| 4,632,100 | 12/1986 | Somers ......................... 128/92 YF |
| 4,659,604 | 4/1987 | Lambuth ...................... 411/457 |
| 4,711,234 | 12/1987 | Vives ............................. 411/469 |
| 4,759,765 | 7/1988 | Van Kampen ................ 128/92 YE |
| 4,772,286 | 9/1988 | Goble ............................. 623/13 |
| 4,793,335 | 12/1988 | Frey ............................... 411/457 |

FOREIGN PATENT DOCUMENTS

2118662 11/1983 United Kingdom ........... 128/92 YC

*Primary Examiner*—Robert A. Hafer
*Assistant Examiner*—Michael Brown
*Attorney, Agent, or Firm*—M. Reid Russell

[57] ABSTRACT

A ligament fixation device and system for its use that includes a channel ligament clamp (10) fabricated for human implantation and consisting of a channel section having a web (13) between parallel sides wherefrom sections have been removed leaving spaced apart pointed spikes (11) that extend outwardly from walls (12), the channel web including a group of pointed pins (15) that extend therefrom parallel and alongside the spikes (11), and at least one screw-type fastener hole (14) formed therethrough. The system of the invention includes tooling for locating a ligament on a bone surface and scoring that surface for drilling. After drilling, a right angle post (22) of a drilling guide (21) is fitted into that drilled hole (20) and the drill guide longitudinal axis is aligned with the ligament location on the bone surface, which drilling guide has an array of spike and pin holes formed therethrough for receiving a drill turned individually therethrough into the bone surface. In practice, the clamp (10) is positioned over the drilled holes, with a ligament under tension therebetween and the pointed pins (15) are driven through the ligament and into the prepared pin holes, preferably utilizing a seating tool (30), and a screw (40) is turned through the web hole (19) and the ligament into the prepared hole (20), to sandwich the ligament that is contained between the clamp spikes (12) against the bone surface.

19 Claims, 5 Drawing Sheets

CHANNEL LIGAMENT CLAMP AND SYSTEM

BACKGROUND OF THE INVENTION

1. Field of the Invention

The present invention relates to devices used in ligament repair and replacement surgery for securing under tension a ligament end to a bone surface.

2. Prior Art

In the area of ligament repair and replacement surgery it has been common to utilize a staple arrangement to attach a ligament end to a bone surface. An example of such staple device and its use is shown in a patent to Shapiro, U.S. Pat. No. 4,414,967. The Shapiro patent illustrates an arrangement where, with tension applied to the ligament end and staple legs positioned to straddle the ligament, the staple legs are driven into the bone with the staple web sandwiching and binding the ligament against the bone.

Examples of other devices for connecting ligament ends to a bone surface or to within a bone are shown in a patent of the present inventors, U.S. Pat. No. 4,632,100, and in a U.S. patent application Ser. No. 015,432, as well as in a patent to one of the present inventors, E. Marlowe Goble, U.S. Pat. No. 4,738,255. Additionally, another example of a ligament anchor system is shown in a United States patent to Hunt, et al., U.S. Pat. No. 4,590,928.

The above cited ligament anchor devices and systems all provide for fixing a ligament to a bone surface or to within a bone during healing where the bone and ligament bond together. This is also the function performed by the channel ligament clamp of the present invention. The present invention, however, provides a superior pull out strength to such earlier devices, particularly staple-type arrangements.

The channel clamp of the present invention provides a number of pointed spikes and pins as well as at least one screw-type coupling. Which pins and screw-type couplings are passed through the ligament and into the bone with the spikes containing the ligament. This arrangement provides a number of points of rigid support through the ligament for clamping it securely to the bone surface. Heretofore, certain fixation devices that have been employed for holding a ligament end onto a bone surface have included a disk or plate to receive a screw therethrough for seating in the bone. Such devices have incorporated spikes that extend from a ligament engaging surface for penetrating to grip the ligament surface but do not pass through the ligament. So arranged, as the screw is turned into the bone, the ligament engaging surface sandwiches the ligament against the bone. Examples of such fixation devices are manufactured by Synthes Canada, Ltd., of Mississauga, Ontario, Canada. These fixation devices, however, by their arrangement of spikes for gripping the ligament surface, do not provide the coupling strength of the channel clamp of the present invention.

BRIEF SUMMARY OF THE INVENTION

It is a principal object of the present invention in a channel ligament clamp and system to provide a device for securely fixing a ligament to a bone surface so as to promote healing.

Another object of the present invention is to provide a system for optimally locating an end of a ligament under tension to a bone surface, and preparing that bone location to receive spikes and pins of a channel clamp and at least one screw-type fastener fitted through the web of that channel clamp, which fastener is turned through the ligament and into the bone, the pins passing through the ligament and into the holes drilled into the bone, for containing the ligament between the spikes and clamping it against the bone surface.

Another object of the present invention is to provide a channel ligament clamp where the channel parallel sides are formed into spaced apart parallel spikes and the channel web includes at least one hole formed therethrough along with a grouping of a plurality of pointed pins extending alongside and parallel to the spikes.

Still another object of the present invention is to provide a system of tooling for: piercing an end of the ligament under tension to score a bone surface; drilling, at that scored location, a hole in the bone to receive a screw-type fastener; and locating and drilling into the bone surface holes to accommodate the spikes and pins of a channel clamp.

Still another object of the present invention is to provide a channel ligament clamp that is easily and reliably positioned to a bone surface to secure a ligament end thereto and to prohibit ligament separation from that bone surface at significantly greater than anticipated tension loads.

In accordance with the above objects, the present invention in a channel ligament clamp is formed from a metal such as titanium that is compatible for human implantation and is of a size such that the channel web will just span an end of a ligament that is to be attached to a bone surface. The channel ligament clamp parallel sides are each formed into spaced apart parallel spikes, and the channel web includes a grouping of pins extending therefrom and parallel to and alongside of the spikes. Which web is also centrally holed to receive a screw-type fastener fitted therethrough for turning through the ligament and into a bone so as to clamp the ligament to the bone surface. In such clamping, the screw-type fastener and pointed ends of the pins will pass through the ligament and into the bone, providing a number of anchor points for the ligament and to the bone, with the spikes, also seated in the bone, containing the ligament therebetween.

The system of the present invention provides tooling for first holing the end of a ligament under tension that is positioned appropriately on a bone surface. During the holing, that bone surfaces is scribed by a tool passed through the ligament for drilling a hole in that bone surface to receive the screw-type coupling. For further preparing this bone, a post portion of a template or drill guide is fitted into that drilled hole and the longitudinal axis of a body portion of that drill guide is aligned over where the ligament longitudinal center axis will be positioned. The drill guide body is appropriately holed to receive a drill turned therethrough that passes into the bone surface, forming holes therein to a depth that is suitable to receive the pointed ends of the channel clamp spikes and pins. The bone surface is thereby prepared to receive the channel clamp fitted thereto.

In practice, a ligament under a desired tension is optimally positioned on a bone surface and a pointed end of a shaft is urged through a lateral midpoint of that ligament, scoring the bone surface. The bone is then drilled at the scored point forming a hole to receive a screw-type fastener to be turned therein. Following the drilling, a pin end of a template or drill guide is fitted therein with the longitudinal axis of which drill guide body to approximately align with a line on the bone surface whereover the ligament longitudinal axis is to be positioned. The bone surface is then drilled through holes in the drill guide to an appropriate depth to receive the pointed ends of the channel clamp pins and spikes.

To attach the ligament to the bone surface the channel ligament clamp is positioned to straddle the ligament such that the hole through the channel ligament clamp web is aligned with the hole formed through the ligament and the screw-type fastener hole drilled into the bone. In this positioning the pins and spikes of the channel ligament clamp will be aligned with the holes that have been formed into the bone surface utilizing the drill guide. A seating tool is then overlaid the channel ligament clamp, which seating tool is holed to receive a tapered shaft that has a pointed end. The seating tool hole to be aligned with and pass the tapered shaft pointed end through the channel ligament clamp web hole, the hole through the ligament, and into the screw-type fastener hole formed into the bone. The tapered shaft opposite end is then struck or otherwise urged to move the shaft pointed end into the bone. In which travel the tapered side of the shaft picks up the seating tool, driving the pins of the channel ligament clamp through the ligament and into the holes formed in the bone surface. The seating tool and shaft are then removed and a screw-type coupling is turned into the bone, locking the channel ligament clamp with the ligament contained between the spikes, sandwiched to the bone surface.

A second channel ligament clamp embodiment can include two spaced apart laterally centered holes formed through the web thereof. Each hole for receiving a screw-type fastener fitted therethrough that is turned into holes prepared in the bone, as set out above.

DESCRIPTION OF THE DRAWINGS

These and other objects and features of the present invention will become more fully apparent from the following description in conjunction with the accompanying drawings.

DETAILED DESCRIPTION

Figure 1:
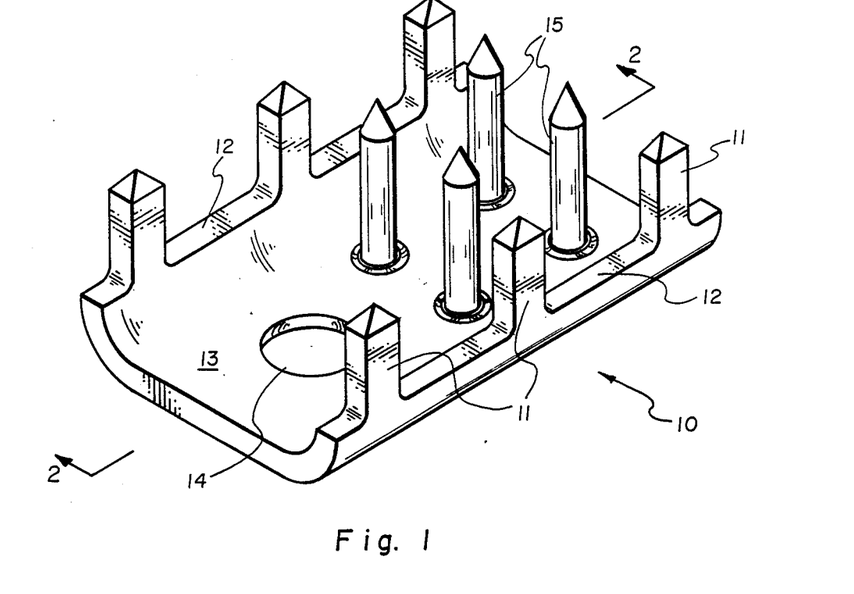
FIG. 1 is a profile perspective view of a first embodiment of a channel ligament clamp of the present invention.
Figure 2:
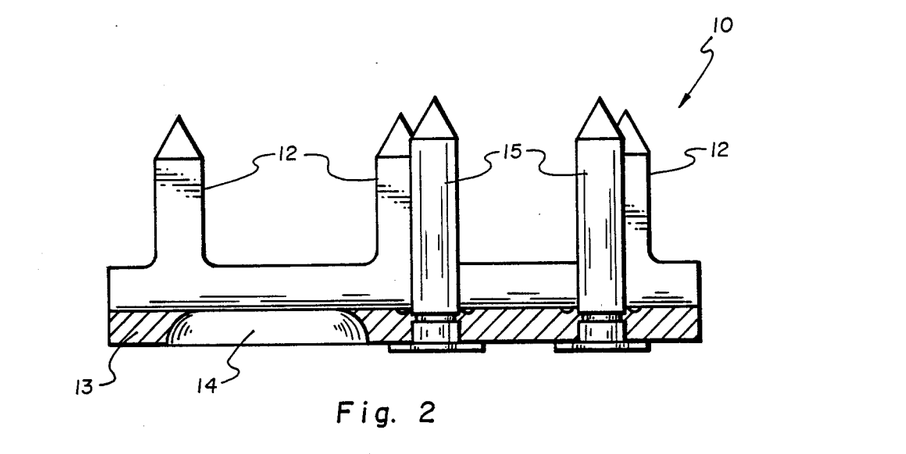
FIG. 2 is a side elevation sectional view taken along the line 2—2 of FIG. 1.

Ligament repair and replacement surgery that involves either biologic grafts or prosthetic ligaments generally require, as part of the procedure, a capability for exactly maintaining the ligament end positioning and tension to a bone surface. The present invention, as shown in FIGS. 1 and 2, is in a channel ligament clamp 10, hereinafter referred to as clamp 10, that is for fixing a ligament under tension to a bone surface. Additional to clamp 10 the present invention also includes tooling and a system for its use for mounting clamp 10 to a bone. The tooling is used for both positioning the ligament and clamp 10 on a bone surface and forming, preferably by drilling, holes into that bone to receive pins and spikes of the clamp with at least one screw-type fastener for maintaining the clamp 10 to the bone, passing through a hole in the clamp web and through the ligament.

FIGS. 1 and 2 show clamp 10 as a channel section having parallel sides that have been formed into spaced apart and parallel pointed spikes 11. Spikes 11 extend outwardly from a top of the channel side walls 12 that are curved through ninety (90) degrees into a web 13 that extends therebetween. Proximate to one end of which web 13, along its longitudinal axis, a hole 14 is formed for receiving a screw-type fastener fitted therethrough for turning into a bone, as will be discussed in detail later herein, particularly with reference to FIGS. 6 and 9.

Shown best in FIGS. 1 and 2, the clamp web 13 further includes a grouping of pins 15. Each pin 15 is shown as having a sharp pointed end, the pins extending parallel to one another, at right angles from that web 13, and are arranged alongside and parallel to spikes 11. Preferably, the pins 15 are slightly longer than the spikes 11 to first contact a ligament surface, as will be set out in detail later herein. In practice, as the clamp 10 is urged onto the ligament, the pins 15 first penetrate and pass through the ligament to travel into holes formed in the bone surface, as will be set out hereinbelow. The clamp spikes 11 to follow the pins 15 into the bone surface for containing the ligament therebetween, as set out in detail hereinbelow.

FIG. 2 shows the clamp 10 as preferably constructed of metal. In practice, titanium metal having a thickness of approximately 0.040 inches has been used successfully in practice, which metal is suitable for human implantation.

Where FIGS. 1 and 2 show a first embodiment of clamp 10 as including four pins 15 that are arranged in a square, each projecting alongside and parallel from the clamp web 13, it should be understood that other numbers and arrangements of pins 15 could be employed within the scope of this disclosure. An example of another pin arrangement is shown as a second channel ligament clamp embodiment in FIG. 9, as will be discussed hereinbelow.

In forming the channel 10, as shown in FIGS. 1 and 2, the unit, less the pins 15, may be formed from a single section of the preferred titanium, or other material as is appropriate for human implantation. Such fabrication may involve forming, as by bending the channel sides each through approximately an 0.08 inch radial bend, whereafter sections of those sides are removed, as by grinding, to leave as remainders the spikes 11. So arranged, the spikes extend co-planar from walls 12, and the ends of which spikes 11 are sharpened. Further, hole 14 and a grouping of pin 15 head holes are formed through the web 13. Of course, the sections of the channel sides and web holes can be removed as by stamping and the spikes 11 and walls 12 then bent to the configuration shown, or the entire clamp 10 can be cast as a single unit, within the scope of this disclosure.

The clamp web 13 with pin head holes formed therethrough, as set out hereinabove, is to receive pins 15 mounted thereto. Preferably, for that mounting, each pin 15 will have a flat head end with a circumferential groove formed around the neck thereof just below the head. The pin 15 is mounted to the web 13 by a creation of a flow of the web metal around the hole into the pin neck circumferential groove. This mounting is preferably accomplished utilizing a staking tool, not shown, where the clamp web 13 is positioned thereon with a pin 15 fitted through that web into a recess in the staking tool. The lip of the staking tool recess is preferably rounded to concentrate a force applied thereto. Thereby, when a compressive pressure is applied to the pin head end, the staking tool lip will tend to urge the metal around the web hole into the pin neck circumferential groove. This metal flow provides a tight permanent coupling of the pin 15 in the clamp web 13. Of course, the clamp 10 could be fabricated by molding methods, from the above set out or other metal, or a hard plastic within the scope of this disclosure. Also, it should be understood, the clamp 10 can be formed in different sizes for accommodating different widths of ligaments.

As set out above, the clamp 10 is for securing a ligament to a bone surface whereby the exact positioning and tensile state of the ligament to the bone is maintained during healing. Accordingly, the present invention also includes tooling and a procedure for its use for: locating a connection point for the ligament on a bone surface; drilling holes into the bone surface for receiving the spikes and pins of the clamp 10 and for receiving at least one screw-type fastener; urging the clamp pins 15 through the ligament into the appropriate prepared holes, the spikes 11 containing the ligament therebetween also passing into the appropriate prepared holes; and turning the screw-type fastener in the hole formed in the bone to permanently maintain the ligament against the bone surface.

Figure 3:
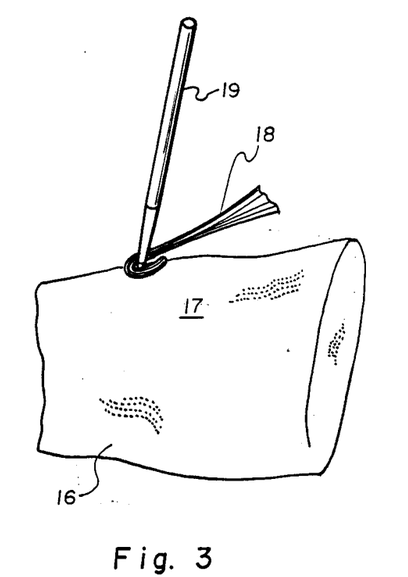
FIG. 3 is a profile perspective view of a bone whereto a ligament is shown aligned to be secured with a pointed end of a shaft passed therethrough to scribe the bone surface.

FIG. 3 shows a bone 16 that could be the side of a tibia having a surface 17 whereto a ligament 18 is shown positioned for attachment to that bone surface with the clamp 10 of the present invention. Ligament 18, it should be understood, can be a natural or biologic graft (allograft or autograft) ligament or a prosthetic ligament.

Figure 4:
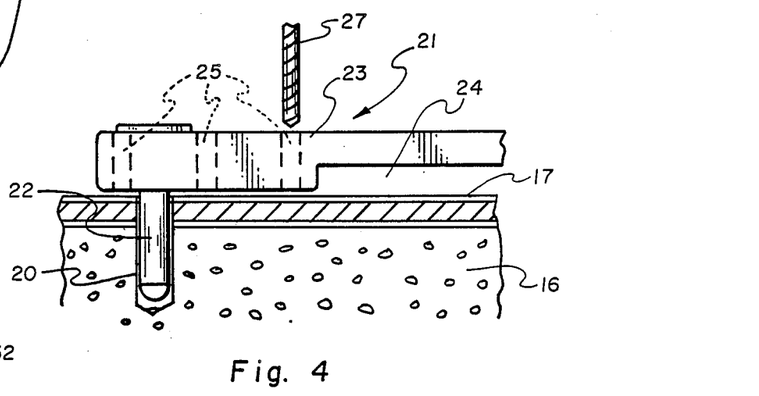
FIG. 4 is a side elevation enlarged sectional view of the bone of FIG. 3 after a hole has been formed into that bone at the scribe point and showing a rounded end of a post of a template or drill guide fitted therein.
Figure 8:
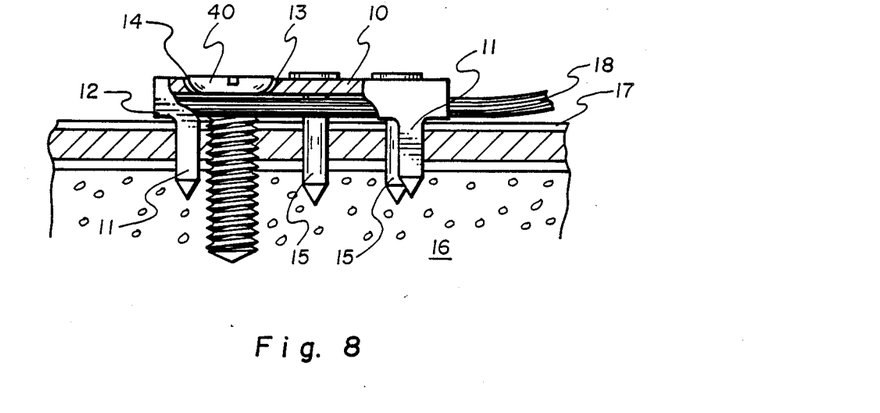
FIG. 8 is a side elevation view of the section of bone of FIG. 4, showing the channel ligament clamp mounted thereto, to sandwich the ligament section of FIG. 6 to the bone surface and shows a screw-type fastener turned through the channel ligament clamp web, ligament and into the bone.

Shown in FIG. 3, ligament 18 is positioned, as by a surgeon performing the procedure, on the bone surface 17, and a desired tensile stress is applied thereto. So arranged, a pointed end of a spike 19, or like pointed tool, is manually urged through the ligament to score the bone surface 17. Thereafter, as illustrated in FIG. 4, the bone surface 17 is drilled at that scored point to form a screw-type fastener hole therein, hereinafter referred to as screw hole. The screw hole 20 is for receiving a screw or like fastener turned therein, as shown in FIG. 8. Also, as illustrated in FIG. 4, screw hole 20 receives a post 22 fitted therein of a template or drill guide 21, hereinafter referred to as drill guide. The post 22 is for use in aligning that drill guide on the bone surface to overlay where the ligament will be positioned and is for forming spike and pin holes therein, as set out immediately below.

Figure 5:
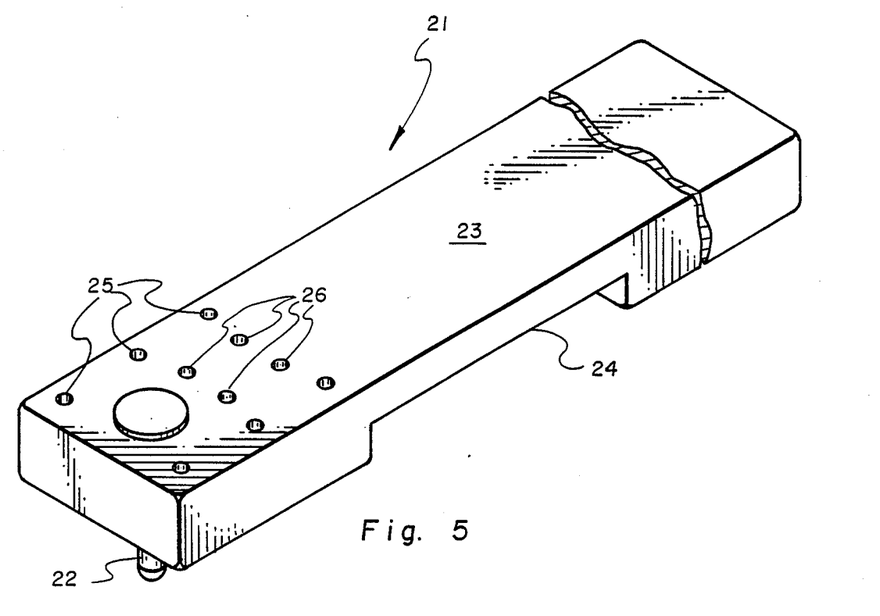
FIG. 5 is a profile perspective view of the template or drill guide of FIG. 4, showing a lateral section removed therefrom.

The drill guide 21, as shown in FIG. 5, preferably has a rectangular body 23, shown as being preferably formed of metal, and has a center lateral slot 24 removed from the undersurface or face thereof as a hand engaging or gripping surface. The rectangular body is shown broken across an end thereof that is opposite to post 22, illustrating that the body 23 can be formed to have a convenient length to facilitate its being held by a surgeon performing the procedure.

The drill guide rectangular body has formed therethrough, parallel rows of spike holes 25, and a cluster of four pin holes 26, shown formed as a square. The respective spike and pin holes, 25 and 26, are to receive, as shown in FIG. 4, a drill 27 turned therethrough that travels into bone 15. Accordingly, a surgeon holding the rectangular body 23, with the post 22 thereof installed, as shown in FIG. 4, in the screw hole 20, can align the longitudinal axis of the rectangular body where the longitudinal axis of the ligament will be positioned, which line will be marked on the surface 17 of bone 16. Drill 27 is turned to form spike holes 28 and pin holes 29 that are at an appropriate depth into the bone surface 17, as shown in FIG. 6, so as to receive the channel spikes 11 and pins 15 pointed ends fitted therein.

Figure 6:
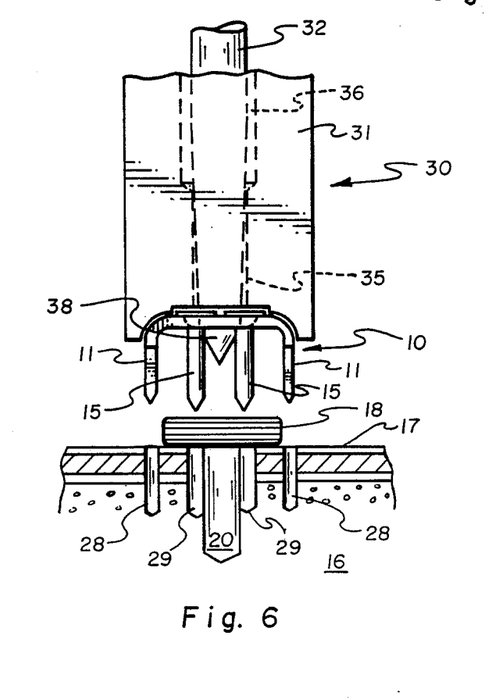
FIG. 6 is an end elevation view of the section of bone of FIG. 4 showing the channel ligament clamp of FIG. 1 aligned thereover with holes formed in the bone to receive channel ligament clamp pins and spikes, with a section of a ligament sandwiched therebetween, and with a seating tool shown positioned thereabove.
Figure 7:
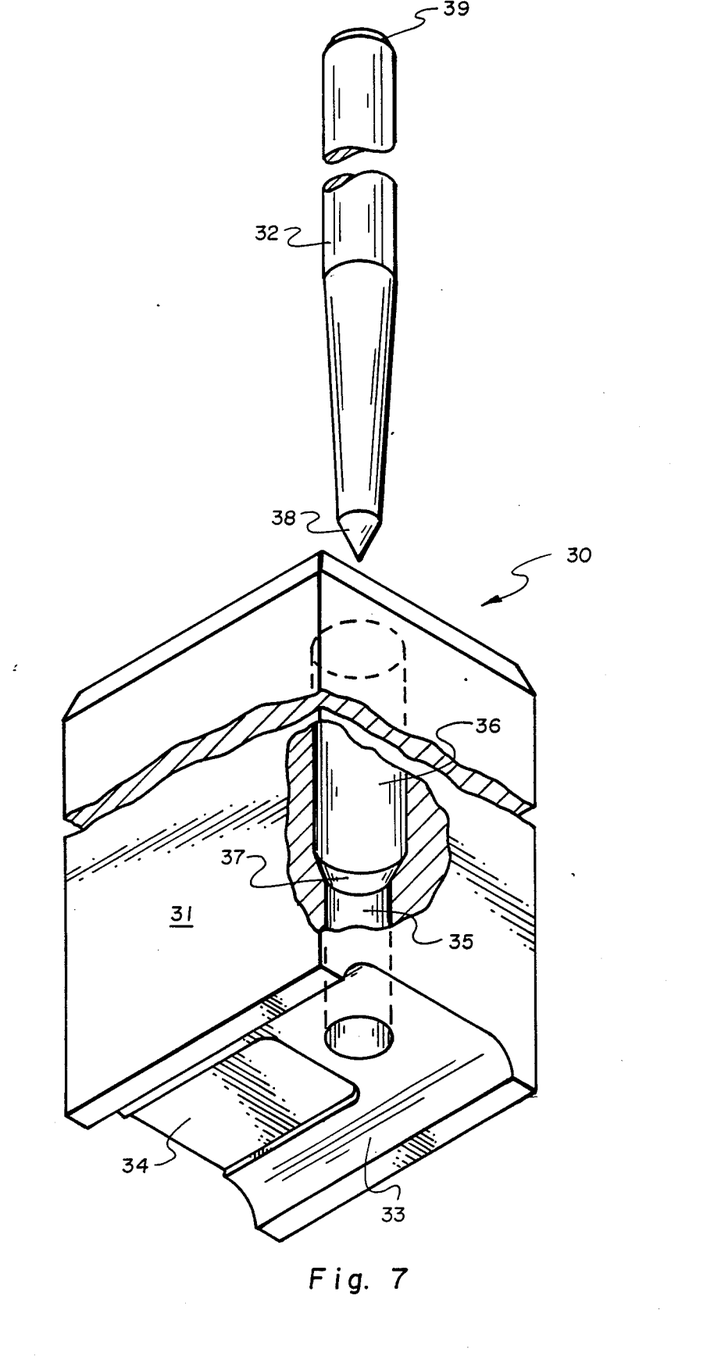
FIG. 7 is a profile perspective view of the seating tool of FIG. 6 showing it as including a tapered pointed shaft aligned for fitting through a vertical stepped hole of the seating tool.

Shown in FIG. 6, the clamp 10 is positioned over bone surface 17 wherethrough spike and pin holes 28 and 29, respectively, have been drilled. Positioned between the clamp 10 and bone surface 17 is shown an end of ligament 18 with a seating tool 30 shown positioned above the clamp. The seating tool consists of a body 31 and a separate tapered shaft 32. The seating tool body 31, as shown in FIG. 7, has a depression 33 formed in the undersurface thereof to just accommodate the clamp 10 web 13 seated therein. The depression 33 is further stepped into the body 31 to form a recess 34. The depression 33 exactly accommodates, as shown in FIG. 6, the top surface of the clamp web 13, with the head ends of pins 15 to fit into recess 34, providing thereby a close and constant contact of the seating tool over the entire clamp web.

Shown in broken lines in FIG. 6 and in a broken away portion of FIG. 7, the seating tool body 31 is drilled therethrough with a hole 35 that is counter sunk to have a greater diameter upper hole portion 36, above a neck 37. The shaft 32, as shown best in FIG. 6, is for fitting through the upper hole 36 to extend through and Just beyond the end of hole 35, whereat the tapered surface of the shaft engages the neck 37. So arranged, shaft 32 pointed end will extend through the clamp web hole 14 and ligament 18 hole, formed by tool 19 as shown in FIG. 3, and travel into screw hole 20. Shown in FIG. 7, the shaft 32 includes a flat upper or top end 39 for striking, as with a hammer, not shown. Striking the shaft top end 39 causes the shaft 32 to travel through the upper hole 36 and hole 35 to where the shaft tapered surface diameter is equal to the diameter at neck 37. Thereafter the body 31 will travel with the shaft such that a force applied to the shaft 32 head end is transmitted through the body 31 and directly into clamp 10.

Shown in FIG. 6, application of a force on the shaft 32 head end will be distributed through the body uniformly onto clamp 10. Guided by the shaft point end 38 that travels through the ligament 18 and into screw hole 20, the clamp pins 15 will first pass through the ligament and then travel into the pin holes 29 formed in the bone surface. The clamp spikes 11, in turn, are to contain the ligament therebetween, with their ends passing into the spike holes 28 formed in the bone surface, to the attitude shown in FIG. 8. FIG. 8 additionally shows a screw 40 as having been fitted through clamp hole 14 and ligament 18 and turned into screw hole 20 of bone 16, sandwiching the ligament 18 against bone surface 17.

FIG. 8 shows screw 40 as being a short screw. Accordingly, the screw 40 will pass through only the one bone surface 17 or cortex. In practice, the number of bone surfaces or cortex passed through is a measure of fastener holding strength. For the arrangement of FIG. 8, the clamp 10 strength is judged as a "purchase of one cortex". Should a longer screw 40 be used where it will turn through the bone 16 and exit the opposite bone surface, then the coupling would qualify as a "purchase of two cortex", indicating a stronger coupling.

Figure 9:
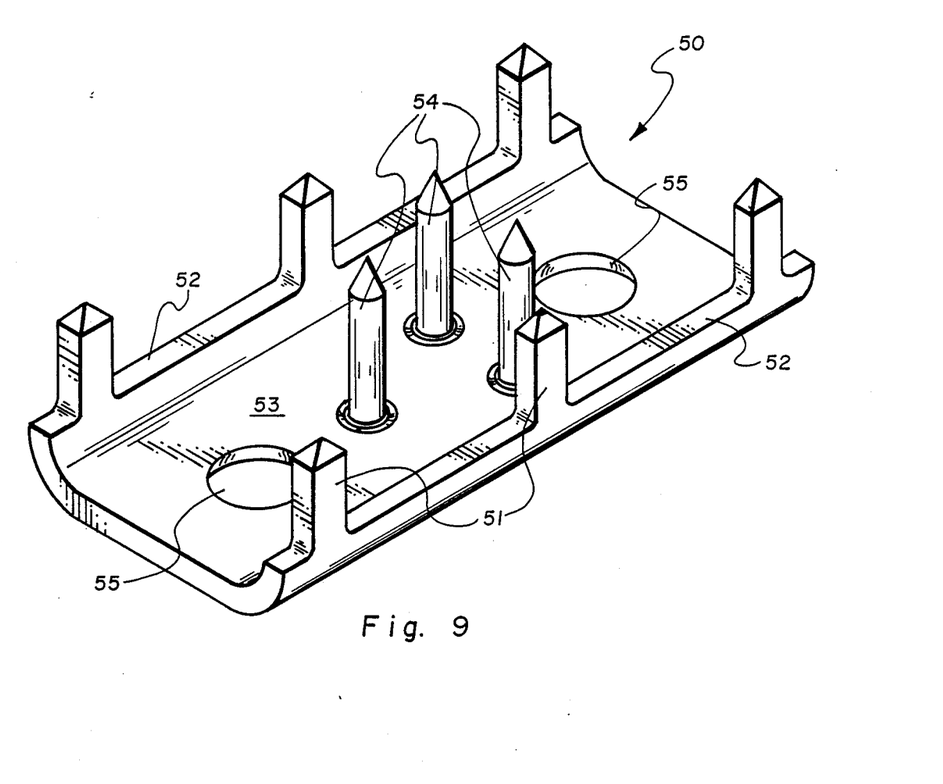
FIG. 9 is a profile perspective view of a second embodiment of a channel ligament clamp of the present invention.

FIG. 9 shows another embodiment of a channel ligament clamp 50, hereinafter referred to as clamp. Clamp 50 is like the above-described clamp 10 in that it is preferably formed from a section of channel of titanium wherefrom sections of the parallel channel sides have been removed leaving pointed spikes 51 that extend outwardly from walls 52, the walls having a web 53 therebetween. Like clamp 10, the web 53 also includes a grouping of pointed pins 54 that extend parallel and alongside spikes 51, which pins 54, in this embodiment, are shown arranged in a triangular grouping. Distinct from clamp 10, clamp 50 includes a pair of holes 55 that are spaced equidistantly from the web opposite ends, and are each centered laterally along the web longitudinal axis. Each hole 55 is to receive a screw-type fastener fitted therethrough and through the bone surface or cortex. Accordingly, clamp 50 allows the surgeon, utilizing short screws to "purchase two cortex," providing a holding strength that is equivalent to use of clamp 10 with a long screw that is passed through the bone to exit the opposite bone surface, or cortex. Further, for added holding strength, long screws can be used with clamp 50 to travel through the bone, exiting the opposite bone surfaces to provide for a "purchase of four cortex".

It should be understood that the installation of clamp 50 is essentially like the procedure described for installing clamp 10 and accordingly the discussion of the installation of clamp 10 should be taken as being essentially the same for clamp 50. Except, of course, that after locating the clamp 50 on the bone surface, over the ligament, a first screw is turned through one hole 55, followed by the turning of a second screw through the second hole 55.

While preferred embodiments of the invention in a channel ligament clamp and system have been shown and described herein, it should be understood that the present disclosure is made by way of example only and that variations to the structure of the channel ligament clamp, tooling, and process are possible within the scope of this disclosure without departing from the subject matter coming within the scope of the following claims, which claims we regard as our invention.

We claim:

1. A channel ligament clamp system for attaching a ligament to a bone surface, that is either a biologic graft or a prostetic ligament, to a bone surface comprising, a pointed instrument for piercing a ligament maintained on a bone surface to score that bone surface therebelow; means for forming a right angle hole into that bone surface at that second point; a channel ligament clamp for human implantation that includes a web between channel sides, which said web includes a plurality of pins that individually extend therefrom and are alongside and parallel to said channel sides, which said web includes at least one laterally centered hole formed therethrough; drill guide means that includes a body with a right angle post extending therefrom, said body including holes formed therethrough that are in the pattern of said channel ligament clamp pins, said drill guide means right angle post for fitting into said hole formed in said bone to position said pin holes appropriately on the bone surface to receive a drill turned therethrough into said bone surface; seating tool means for locating said channel ligament clamp web hole over said hole that is formed through said ligament and said hole formed in the bone and said seating tool means for urging said channel ligament clamp pins through said ligament to enter the pin holes drilled into said bone surface; and a screw-type fastener means for turning through said aligned web and ligament holes and into said bone, sandwiching said ligament against said bone surface between said channel sides.

2. A ligament clamp system as recited in claim 1, wherein the pins are arranged in a group that is located proximate to one web end, with each pin equidistant from the web longitudinal axis.

3. A ligament clamp system as recited in claim 2, wherein the pin grouping is a square.

4. A ligament clamp system as recited in claim 1, wherein the channel ligament clamp web has two longitudinally aligned laterally centered holes formed therethrough separated by a grouping of pins extending therefrom.

5. A ligament clamp system as recited in claim 4, wherein the pins are arranged in a triangle configuration with one pin located on the web longitudinal axis and with the remaining pins that form the triangle spaced equidistantly from that axis.

6. A ligament clamp system as recited in claim 1, wherein the channel ligament clamp is fabricated out of titanium.

7. A ligament clamp system as recited in claim 1, wherein the drill guide body means includes means for aligning its longitudinally axis with the position on the bone surface whereon the ligament will rest.

8. A ligament clamp system as recited in claim 1, wherein the seating tool means consist of a rectangular block that includes a depression on a lower surface that is of a shape to accommodate the channel ligament clamp nesting therein, and includes a vertical hole formed therethrough that will align with the hole formed through the web of said channel ligament clamp, which said vertical hole is stepped outwardly from the lesser diameter adjacent to the depression to a greater diameter thereabove; and a shaft means that is tapered outwardly from a pointed end to a diameter that is greater than said lesser diameter portion of said vertical hole, said shaft means having a flat upper end surface.

9. A ligament clamp system as recited in claim 1, wherein the screw-type fastener is a short screw to be turned through only one bone surface.

10. A ligament clamp system as recited in claim 1, wherein the screw-type fastener is a long screw that is to be turned through opposing bone cortex surfaces.

11. A channel ligament clamp comprising, a section of channel constructed from a material suitable for human implantation having upstanding spaced apart parallel channel sides with a web therebetween to fit over a ligament said web having inner and outer surfaces; pin means consisting of a plurality of pins, each pin having a cylindrical shaft with a pointed end and an enlarged broad head opposite end, which said cylindrical shaft includes a circumferential groove formed around said cylindrical shaft, spaced apart from said broad head, said pin fitted through a hole in said web, said circumferential groove located adjacent to and just below said web inner face surface, said pin extending alongside and parallel to said channel sides, said circumferential grooves, each receiving a metal flow from around holes formed through said web, staking each said pin in said web; and at least one laterally centered hole formed through said web for receiving a screw-type fastener fitted therethrough.

12. A channel ligament clamp as recited in claim 1, wherein the channel sides are arranged as spikes, said spikes and pins each have pointed ends and the pins are slightly longer than the spikes.

13. A channel ligament clamp as recited in claim 11, wherein the pins are arranged equidistant from and along opposite sides of the web longitudinal axis in a grouping that is proximate to one web end, with the laterally centered hole formed through said web proximate to the other web end.

14. A channel ligament clamp as recited in claim 11, wherein the pins are arranged n a triangular pattern at approximately the web center, one pin on and the other pins straddling the web longitudinal axis; and a pair of laterally centered holes formed through said web, each proximate to a web end.

15. A channel ligament clamp as recited in claim 11, wherein the channel section and pins are formed out of titanium.

16. A method for securing a ligament to a bone surface comprising the steps of, locating a ligament under a desired tension on a bone surface; with a sharp end of a tool, piercing the ligament to score said bone surface; drilling an appropriate diameter fastener hole into the bone; with a drill guide having a body that includes an array of holes formed therethrough that conform to the size and spacing of parallel pins of a channel ligament clamp, positioning said drill guide over the ligament location on the bone surface, and drilling said bone surface through each of said array of pin holes to a depth that is appropriate to receive the ends of said channel ligament clamp pins; fitting said channel ligament clamp over said ligament positioned above the holes that were formed in said bone surface utilizing said drill guide such that said channel ligament clamp ends align to said formed holes; utilizing a seating tool means that provides for fitting a pointed end of a shaft through said channel ligament clamp web, said ligament and said fastener hole that has been formed into said bone surface, urging said channel ligament clamp towards said bone surface such that said pin ends thereof pass through said ligament contained between said channel ligament clamp sides, which said pin ends pass into said pin holes that have been drilled into said bone surface; and turning a screw through the channel ligament clamp web hole, ligament and into said fastener hole that has been formed into said bone surface.

17. A procedure as recited in claim 16, wherein the screw is sufficiently long to pass through the entire bone, exiting from an opposite bone surface.

18. A method as recited in claim 16, wherein the channel ligament clamp has a pair of spaced apart holes formed therethrough each for receiving a screw turned therethrough.

19. A method as recited in claim 18, wherein one or both screws is of sufficient length to pass entirely through the bone to exit an opposite bone surface.

* * * * *